US010725051B2

(12) United States Patent
Krizman et al.

(10) Patent No.: US 10,725,051 B2
(45) Date of Patent: Jul. 28, 2020

(54) MULTIPLEX MRM ASSAY FOR EVALUATION OF CANCER

(71) Applicant: NantOmics, LLC, Culver City, CA (US)

(72) Inventors: David B. Krizman, Gaithersburg, MD (US); Todd Hembrough, Gaithersburg, MD (US); Sheeno Thyparambil, Frederick, MD (US); Wei-Li Liao, Herndon, VA (US)

(73) Assignee: Expression Pathology, Inc., Rockville, MD (US)

( * ) Notice: Subject to any disclaimer, the term of this patent is extended or adjusted under 35 U.S.C. 154(b) by 0 days.

(21) Appl. No.: 16/160,680

(22) Filed: Oct. 15, 2018

(65) Prior Publication Data

US 2019/0033320 A1 Jan. 31, 2019

Related U.S. Application Data

(60) Division of application No. 15/174,970, filed on Jun. 6, 2016, now Pat. No. 10,101,334, which is a division of application No. 14/223,524, filed on Mar. 24, 2014, now Pat. No. 9,360,487, which is a continuation of application No. PCT/US2012/056965, filed on Sep. 24, 2012.

(60) Provisional application No. 61/537,918, filed on Sep. 22, 2011.

(51) Int. Cl.
*G01N 33/68* (2006.01)
*G01N 33/74* (2006.01)
*G01N 33/574* (2006.01)

(52) U.S. Cl.
CPC ... *G01N 33/6848* (2013.01); *G01N 33/57415* (2013.01); *G01N 33/6893* (2013.01); *G01N 33/743* (2013.01); *G01N 2333/47* (2013.01); *G01N 2333/70567* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| 7,473,532 | B2 | 1/2009 | Darfler et al. |
| 7,588,887 | B2 | 9/2009 | Franza, Jr. et al. |
| 9,360,487 | B2 * | 6/2016 | Krizman ............ G01N 33/6893 |
| 10,101,334 | B2 * | 10/2018 | Krizman ............ G01N 33/6893 |
| 2009/0136971 | A1 | 5/2009 | Krizman et al. |
| 2011/0178273 | A1 | 7/2011 | Aabersold et al. |
| 2014/0199717 | A1 | 7/2014 | Krizman et al. |

FOREIGN PATENT DOCUMENTS

| CN | 1920036 A | 2/2007 |
| JP | 2004192257 A | 7/2004 |
| JP | 2008527045 A | 7/2008 |
| WO | 2006127861 A2 | 11/2006 |
| WO | 2011028960 A1 | 3/2011 |
| WO | 2011087865 A1 | 7/2011 |
| WO | 2012083338 A1 | 6/2012 |

OTHER PUBLICATIONS

Atsriku et al.: "Systemic Mapping of Posttranslational Modifications in Human Estrogen Receptor-[alpha] with Emphasis on Novel Phosphorylation Sites", Molecular & Cellular Proteomics, vol. 8, No. 3, Nov. 3, 2008 pp. 467-480.
Domanski, et al.: "Assay Development for the Determination of Phosphorylation Stoichiometry Using Multiple Reaction Monitoring Methods with and without Phosphatase Treatment: Application to Breast Cancer Signaling Pathways", Analytical Chemistry, vol. 32, No. 13, Jun. 4, 2010, pp. 5610-5620.
European Search Report for Application EP12833172.5; Applicant Expression Pathology, Inc.; dated Apr. 7, 2015; pp. 8.
Extended European Search Report for European Application No. 12833172.5, dated Aug. 14, 2015, 13 pages.
Harvey et al: "Estrogen Receptor Status by Immunohistochemistry is Superior to the Ligand-Binding Assay for Predicting Response to Adjuvant Endocrine Therapy in Breast Cancer," Journal of Clinical Oncology, May 1999, vol. 17, No. 5, pp. 1474-1481.
International Search Report and Written Opinion for International Application PCT/US12/56965, Applicant Expression Pathology, Inc., dated Jun. 18, 2013, pp. 14.

(Continued)

*Primary Examiner* — Sergio Coffa
(74) *Attorney, Agent, or Firm* — Harness Dickey & Pierce P.L.C.

(57) ABSTRACT

The current disclosure provides specific peptides, and derived ionization characteristics of the peptides from the estrogen receptor (ER), progesterone receptor (PR), and/or antigen Ki67 (Ki67) proteins that are particularly advantageous for quantifying the ER, PR, and/or Ki67 proteins directly in biological samples that have been fixed in formalin by the method of Selected Reaction Monitoring/Multiple Reaction Monitoring (SRM/MRM) mass spectrometry. Such biological samples are chemically preserved and fixed wherein the biological sample is selected from tissues and cells treated with formaldehyde containing agents/fixatives including formalin-fixed tissue/cells, formalin-fixed/paraffin embedded (FFPE) tissue/cells, FFPE tissue blocks and cells from those blocks, and tissue culture cells that have been formalin fixed and or paraffin embedded. A protein sample is prepared from a biological sample using the Liquid Tissue™ reagents and protocol, and the ER, PR, and/or Ki67 proteins are quantitated in the Liquid Tissue™ sample by the method of SRM/MRM mass spectrometry by quantitating in the protein sample at least one or more of the peptides described for one or more of the ER, PR, and/or Ki67 proteins. These peptides can be quantitated if they reside in a modified or in an unmodified form. An example of a modified form of an ER, PR, and/or Ki67 peptide is phosphorylation of a tyrosine, threonine, serine, and/or other amino acid residues within the peptide sequence.

17 Claims, No Drawings
Specification includes a Sequence Listing.

(56) References Cited

OTHER PUBLICATIONS

Mukai et al.: "Rapid modulation of long-term depression and spinogenesis via synaptic estrogen receptors in hippocampal principal neurons," Journal of Neurochemistry, Feb. 2007, vol. 100, No. 4, pp. 950-967.
Pedram, et al.: Nature of Functional Estrogen Receptors at the Plasma Membrane (Mol Endocrinol, vol. 20, No. 9, Sep. 2006, pp. 1996-2009.
Whiteaker, et al.: "Integrated Pipeline for Mass Spectrometry-Based discovery and Confirmation of Biomarkers Demonstrated in a Mouse Model of Breast Cancer", Journal of Proteome Research, vol. 6, No. 10, Aug. 21, 2007, pp. 3962-3975.
Australian Examination Report dated Jan. 25, 2017 issued in Australian Patent Application No. 2012311983, 4 pages.
Australian Certificate of Grant dated Jun. 7, 2018 issued in Australian Patent No. 2012311983, 1 page.
Canadian Office Action dated Jul. 25, 2017 issued in Canadian Patent Application No. 2,849,301, 7 pages.
Canadian Office Action dated Jul. 12, 2018 issued in Canadian Patent Application No. 2,849,301, 3 pages.
European Office Action dated Sep. 19, 2017 issued in European Patent Application No. 12 833 172.5, 5 pages.
European Intention to Grant dated Aug. 31, 2018 issued in European Patent Application No. 12 833 172.5, 7 pages.
Israeli Office Action dated Jun. 13, 2018 issued in Israeli Patent Application No. 231600 (with English translation), 8 pages.
Non-final Office Action dated Feb. 26, 2015 issued in U.S. Appl. No. 14/223,524.
Final Office Action dated Aug. 26, 2015 issued in U.S. Appl. No. 14/223,524.
Non-final Office Action dated Nov. 24, 2017 issued in U.S. Appl. No. 15/174,970.
Becker, K-F., et al., "Quantitative protein analysis from formalin-fixed tissues: implications for translational clinical research and nanoscale molecular diagnosis," J Pathol., 211: 370-378 (2007).
Extended European Search Report from European Application No. 19159341.7 dated May 27, 2019.

* cited by examiner

SEQUENCE LISTING

```
<160> NUMBER OF SEQ ID NOS: 10

<210> SEQ ID NO 1
<211> LENGTH: 12
<212> TYPE: PRT
<213> ORGANISM: Homo sapiens

<400> SEQUENCE: 1

Leu Ala Gln Leu Leu Leu Ile Leu Ser His Ile Arg
1               5                   10

<210> SEQ ID NO 2
<211> LENGTH: 11
<212> TYPE: PRT
<213> ORGANISM: Homo sapiens

<400> SEQUENCE: 2

Leu Leu Phe Ala Pro Asn Leu Leu Leu Asp Arg
1               5                   10

<210> SEQ ID NO 3
<211> LENGTH: 11
<212> TYPE: PRT
<213> ORGANISM: Homo sapiens

<400> SEQUENCE: 3

Ala Gly Leu Thr Leu Gln Gln Gln His Gln Arg
1               5                   10

<210> SEQ ID NO 4
<211> LENGTH: 14
<212> TYPE: PRT
<213> ORGANISM: Homo sapiens

<400> SEQUENCE: 4

Val Leu Leu Leu Leu Asn Thr Ile Pro Leu Glu Gly Leu Arg
1               5                   10

<210> SEQ ID NO 5
<211> LENGTH: 12
<212> TYPE: PRT
<213> ORGANISM: Homo sapiens

<400> SEQUENCE: 5

Val Gly Asp Ser Ser Gly Thr Ala Ala Ala His Lys
1               5                   10

<210> SEQ ID NO 6
<211> LENGTH: 11
<212> TYPE: PRT
<213> ORGANISM: Homo sapiens

<400> SEQUENCE: 6

Leu Asp Leu Thr Glu Asn Leu Thr Gly Ser Lys
1               5                   10

<210> SEQ ID NO 7
<211> LENGTH: 11
```

```
<212> TYPE: PRT
<213> ORGANISM: Homo sapiens8

<400> SEQUENCE: 7

Val Glu Pro Val Gly Asp Val Val Ser Thr Arg
1               5                   10

<210> SEQ ID NO 8
<211> LENGTH: 12
<212> TYPE: PRT
<213> ORGANISM: Homo sapiens

<400> SEQUENCE: 8

Ala Ala Asn Leu Trp Pro Ser Pro Leu Met Ile Lys
1               5                   10

<210> SEQ ID NO 9
<211> LENGTH: 17
<212> TYPE: PRT
<213> ORGANISM: Homo sapiens

<400> SEQUENCE: 9

Asn Val Val Pro Leu Tyr Asp Leu Leu Leu Glu Met Leu Asp Ala His
1               5                   10                  15

Arg

<210> SEQ ID NO 10
<211> LENGTH: 6
<212> TYPE: PRT
<213> ORGANISM: Homo sapiens

<400> SEQUENCE: 10

Ser Leu Pro Gly Phe Arg
1               5
```

MULTIPLEX MRM ASSAY FOR EVALUATION OF CANCER

This application is a divisional of U.S. application Ser. No. 15/174,970, filed Jun. 6, 2016, which is a divisional of application Ser. No. 14/223,524, filed Mar. 24, 2013, which is a continuation of International Application No. PCT/US12/56965, filed Sep. 24, 2012, which claims priority to U.S. Application Ser. No. 61/537,918, filed Sep. 22, 2011, entitled "Multiplex MRM Assay for Evaluation of Cancer," the contents of each of which are hereby incorporated by reference in their entireties. This application also contains a sequence listing submitted electronically via EFS-web, which serves as both the paper copy and the computer readable form (CRF) and consists of a file entitled "SeqListing 3900 0008DV2", which was created on Oct. 15, 2018, which is 2,066 bytes in size, and which is also incorporated by reference in its entirety.

INTRODUCTION

Specific peptides derived from subsequences of the estrogen receptor (ER), the progesterone receptor (PR), and the antigen Ki67 (Ki67) proteins are provided. The peptide sequences and fragmentation/transition ions for each peptide are particularly useful in a mass spectrometry-based Selected Reaction Monitoring (SRM), which also can be referred to as a Multiple Reaction Monitoring (MRM) assay. Such assays are alternatively referred to herein as SRM/MRM. Information about the use (individually, simultaneously, or in various combinations) of peptides for SRM/MRM quantitative analysis of these proteins is described.

Results from the SRM/MRM assays can be used to measure relative or absolute quantitative levels of one or more of the specific peptides from (ER), the progesterone receptor (PR), and the antigen Ki67 (Ki67) proteins. Where the proteins are analyzed individually, simultaneously, or in various combinations the assays can be used to correlate accurate and precise quantitative levels of the proteins within specific breast tissue samples (e.g., cancer tissue sample), or any other tissue of origin other than breast, of the patient or subject from whom the tissue (biological sample) was collected and preserved. This not only provides diagnostic information about the breast cancer, but also permits a physician or other medical professional to determine appropriate therapy for the breast cancer patient. Such an assay that provides diagnostically and therapeutically important information about levels of protein expression in a diseased tissue or other patient sample is termed a "companion diagnostic" assay. For example, such an assay can be designed to diagnose the stage or degree of a breast cancer, or any other cancer, and determine a therapeutic agent to which a patient is most likely to respond.

SUMMARY

The assays described herein are assays for measuring relative or absolute levels of specific unmodified peptides from the ER, PR, and the Ki67 proteins. Also, described herein are assays for measuring absolute or relative levels of specific modified peptides from the ER, PR, and Ki67 proteins. Examples of modifications include phosphorylated amino acid residues (e.g. phosphotyrosine, phosphoserine and phosphothreonine) and glycosylated amino acid residues (e.g. glycosylated asparagine residues) that are present on the peptides.

Relative quantitative levels of the ER, PR, and Ki67 proteins are determined by the SRM/MRM methodology, for example, by comparing SRM/MRM signature peak areas (for example, signature peak area or integrated fragment ion intensity) of an individual ER, PR, and/or Ki67 peptide in different samples. Alternatively, it is possible to compare multiple SRM/MRM signature peak areas for multiple ER, PR, and/or Ki67 signature peptides, where each peptide has its own specific SRM/MRM signature peak, to determine the relative ER, PR, and/or Ki67 protein content in one biological sample with the ER, PR, and/or Ki67 protein content in one or more additional or different biological samples. In this way, the amount (or level) of a particular peptide, or peptides, from the ER, PR, and/or Ki67 proteins, and therefore the amount of the ER, PR, and/or Ki67 proteins, is determined relative to the same ER, PR, and/or Ki67 peptide, or peptides, across 2 or more biological samples under the same experimental conditions. In addition, relative quantitation can be determined for a given peptide, or peptides, from the ER, PR, and/or Ki67 proteins within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the ER, PR, and/or Ki67 proteins, and therefore the amount of the ER, PR, and/or Ki67 protein, is determined relative one to another within the same sample. These approaches generate quantitation of an individual peptide, or peptides, from the ER, PR, and/or Ki67 proteins to the amount of another peptide, or peptides, between samples and within samples wherein the amounts as determined by peak area are relative one to another, regardless of the absolute weight to volume or weight to weight amounts of the ER, PR, and/or Ki67 peptide, or peptides, in the protein preparation from the biological sample. Relative quantitative data about individual signature peak areas between different samples are normalized to the amount of protein analyzed per sample. Relative quantitation can be performed across many peptides from multiple proteins and the ER, PR, and/or Ki67 proteins individually or simultaneously in a single sample and/or across many samples to gain insight into relative protein amounts, one peptide/protein with respect to other peptides/proteins.

Absolute quantitative levels of the ER, PR, and/or Ki67 proteins are determined by, for example, the SRM/MRM methodology whereby the SRM/MRM signature peak area of an individual peptide from the ER, PR, and/or Ki67 proteins in one biological sample is compared to the SRM/MRM signature peak area of an exogenously added "spiked" internal standard. In one embodiment, the internal standard is a synthetic version of the same exact ER, PR, and/or Ki67 peptide that contains one or more amino acid residues labeled with one or more heavy isotopes. Suitable isotope labeled internal standards are synthesized so that when analyzed by mass spectrometry it generates a predictable and consistent SRM/MRM signature peak that is different and distinct from the native ER, PR, and/or Ki67 peptide signature peak and which can be used as a comparator peak. Thus, when the internal standard is spiked in a known amount into a protein preparation from a biological sample and analyzed by mass spectrometry, the SRM/MRM signature peak area of the native peptide from the sample can be compared to the SRM/MRM signature peak area of the internal standard peptide. This numerical comparison provides either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to aid in determining which therapeutic agent would be most advantageous for use in treating that patient. Cancer tissue, including breast cancer tissue, that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of an individual protein such as ER, or multiple proteins such as ER, PR, and/or Ki67 can be determined, individually or in a simultaneous fashion, and compared to a "normal" or reference level for each protein or collections of proteins found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer.

Assays of protein levels (e.g., ER, PR, and/or Ki67 levels) can also be used to diagnose the stage of cancer, including breast cancer, in a patient or subject diagnosed with cancer by employing the ER, PR, and/or Ki67 levels. Levels or amounts of proteins or peptides can be defined as the quantity expressed in moles, mass or weight of a protein or peptide determined by the SRM/MRM assay. The level or amount may be normalized to total the level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding ER, PR, and/or Ki67 can thus be used to aid in determining stage or grade of a cancer by correlating the level of the ER, PR, and/or Ki67 proteins (or fragment peptides of the ER, PR, and/or Ki67 proteins) with levels observed in normal tissues.

Once the stage and/or grade, and/or ER, PR, and/or Ki67 protein expression characteristics of the cancer, including breast cancer, has been determined, that information can be matched to a list of therapeutic agents (chemical and biological) developed to specifically treat cancer tissue that is characterized by, for example, abnormal expression of the protein or protein(s) (e.g., ER, PR, and/or Ki67) that were assayed. Matching information from an ER, PR, and/or Ki67 protein assay to a list of therapeutic agents that specifically targets, for example, the ER, PR, and/or Ki67 protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions. These proteins (ER, PR, and/or Ki67) can be used individually, doubly, or all three (3) simultaneously in a personalized medicine approach to not only breast cancer but any other cancer as well. This collection of proteins is most advantageously applied to breast cancer diagnosis and treatment.

These and other aspects of the present disclosure will become apparent to the skilled person in view of the description set forth below.\

DETAILED DESCRIPTION

The Selected Reaction Monitoring/Multiple Reaction Monitoring (SRM/MRM) assay can be used to measure relative or absolute quantitative levels of one or more of the specific peptides from the ER, PR, and/or Ki67 proteins, individually, in combinations, or simultaneously, and therefore provide a means of measuring the amount of the ER, PR, and/or Ki67 proteins in a given protein preparation obtained from a biological sample by mass spectrometry.

More specifically, the SRM/MRM assay can measure these peptides directly in complex protein lysate samples prepared from cells procured from patient tissue samples, such as formalin fixed cancer patient tissue. Methods of preparing protein samples from formalin fixed tissue are described in U.S. Pat. No. 7,473,532, the contents of which are hereby incorporated by references in their entireties. The methods described in U.S. Pat. No. 7,473,532 may conveniently be carried out using Liquid Tissue™ reagents and protocol available from Expression Pathology Inc. (Rockville, Md.).

The most widely and advantageously available form of tissues from cancer patients tissue is formalin fixed, paraffin embedded tissue. Formaldehyde/formalin fixation of surgically removed tissue is by far and away the most common method of preserving cancer tissue samples worldwide and is the accepted convention for standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

In principle, any predicted peptide derived from the ER, PR, and/or Ki67 proteins, prepared for example by digesting with a protease of known specificity (e.g. trypsin), can be used as a surrogate reporter to determine the abundance of ER, PR, and/or Ki67 proteins in a sample using a mass spectrometry-based SRM/MRM assay. Similarly, any predicted peptide sequence containing an amino acid residue at a site that is known to be potentially modified in the ER, PR, and/or Ki67 proteins also might potentially be used to assay the extent of modification of the ER, PR, and/or Ki67 proteins in a sample.

According to one embodiment, ER, PR, and/or Ki67 fragment peptides may be generated in a variety of ways including using Liquid Tissue™ protocol described, for example, in U.S. Pat. No. 7,473,532. Liquid Tissue™ protocol and reagents produce peptide samples suitable for mass spectroscopic analysis from formalin fixed paraffin embedded tissue by proteolytic digestion of the proteins in the tissue/biological sample. Suitable reagents and protocols also are commercially available from OncoPlexDx (formerly Expression Pathology Inc., Rockville, Md.).

In the Liquid Tissue™ protocol the tissue/biological is heated in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent). Following heat treatment the tissue/biological sample is treated with one or more proteases, including but not limited to trypsin, chymotrypsin, pepsin, and endoproteinase Lys-C for a time sufficient to disrupt the tissue and cellular structure of the biological sample and to liquefy the sample. Exemplary conditions for the protease treatment are from 30 minutes to 24 hours at a temperature from 37° C. to 65° C.). Advantageously, endoproteases, and particularly combinations of two or three endoproteases, used either simultaneously or sequentially, are employed to liquefy the sample. For example, suitable combinations of proteases can include, but are not limited to, combinations of trypsin, endoproteinase Lys-C and chemotrypsin, such as trypsin and endoproteinase Lys-C. The result of the heating and proteolysis is a liquid, soluble, dilutable biomolecule lysate. Advantageously, this liquid lysate is free of solid or particulate matter that can be separated from the lysate by centrifugation.

Surprisingly, it was found that many potential peptide sequences from the ER, PR, and/or Ki67 proteins are unsuitable or ineffective for use in mass spectrometry-based SRM/MRM assays for reasons that are not immediately evident. As it was not possible to predict the most suitable peptides for MRM/SRM assay, it was necessary to experimentally identify modified and unmodified peptides in actual Liquid Tissue™ lysates to develop a reliable and accurate SRM/MRM assay for the ER, PR, and/or Ki67 proteins. While not wishing to be bound by any theory, it is believed that some peptides might, for example, be difficult to detect by mass spectrometry because they do not ionize well or produce fragments that are not distinct from those generated from other proteins. Peptides may also fail to resolve well in separation (e.g., liquid chromatography), or may adhere to glass or plastic ware.

ER, PR, and/or Ki67 peptides found in various embodiments of this disclosure (e.g., Tables 1 and 2 below) were derived from the ER, PR, and/or Ki67 proteins by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the ER, PR, and/or Ki67 proteins that are detected and analyzed by mass spectrometry. Identification of a specific preferred subset of peptides for mass-spectrometric analysis is based on: 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue™ reagents and protocol. This entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, such as, trypsin. The skilled artisan will recognize that other proteases, and in particular, endoproteases may be used in place of, or in addition to, trypsin. Each protein lysate was used to prepare a collection of peptides by digestion of intact polypeptides with the protease or protease combination. Each protein lysate is used to prepare a collection of peptides by digestion of intact polypeptides with the protease or protease combination. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is employed. Ion trap mass spectrometers may, however, be the best type of mass spectrometer for conducting global profiling of peptides. Although SRM/MRM assays can be developed and performed on any type of mass spectrometer, including a MALDI, ion trap, or triple quadrupole is an advantageous instrument platform for SRM/MRM assays is often considered to be a triple quadrupole instrument platform.

Once as many peptides as possible were identified in a single mass spectrometric analysis of a single lysate under the conditions employed, then the list of identified peptides was collated and used to determine the proteins that were detected in that lysate. This process was repeated for multiple Liquid Tissue™ lysates, and the very large list of peptides was collated into a single dataset. The resulting dataset represents the peptides that can be detected in the type of biological sample that was analyzed (after protease digestion), and specifically in a Liquid Tissue™ lysate of the biological sample, and thus includes the peptides for specific proteins, such as for example the ER, PR, and/or Ki67 proteins.

In one embodiment, the ER, PR, and/or Ki67 tryptic peptides identified as useful in the determination of absolute or relative amounts of the ER, PR, and/or Ki67 proteins include one or more, two or more, three or more, four or more, five or more, six or more, eight or more, or nine or more of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and/or SEQ ID NO:10, each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more, five or more, six or more, eight or more, or ten or more of those peptides recited in Table 1, and particularly combinations with the peptides found in Table 2) are candidates for use in quantitative SRM/MRM assay for the ER, PR, and/or Ki67 proteins in human biological samples, including directly in formalin fixed patient tissue, and more specifically in formalin fixed breast cancer patient tissue. Table 2 shows additional information regarding some of the peptides shown in Table 1.

TABLE 1

| SEQ ID | Peptide Sequence |
|---|---|
| SEQ ID NO: 1 | Leu Ala Gln Leu Leu Leu Ile Leu Ser His Ile Arg |
| SEQ ID NO: 2 | Leu Leu Phe Ala Pro Asn Leu Leu Leu Asp Arg |
| SEQ ID NO: 3 | Ala Gly Leu Thr Leu Gln Gln Gln His Gln Arg |
| SEQ ID NO: 4 | Val Leu Leu Leu Leu Asn Thr Ile Pro Leu Glu Gly Leu Arg |
| SEQ ID NO: 5 | Val Gly Asp Ser Ser Gly Thr Ala Ala Ala His Lys |
| SEQ ID NO: 6 | Leu Asp Leu Thr Glu Asn Leu Thr Gly Ser Lys |
| SEQ ID NO: 7 | Val Glu Pro Val Gly Asp Val Val Ser Thr Arg |
| SEQ ID NO: 8 | Ala Ala Asn Leu Trp Pro Ser Pro Leu Met Ile Lys |
| SEQ ID NO: 9 | Asn Val Val Pro Leu Tyr Asp Leu Leu Leu Glu Met Leu Asp Ala His Arg |
| SEQ ID NO: 10 | Ser Leu Pro Gly Phe Arg |

TABLE 2

| SEQ ID | Peptide sequence | Mono Isotopic Mass | Precursor Charge State | Precursor m/z | Transition m/z | Ion Type |
|---|---|---|---|---|---|---|
| SEQ ID NO: 1 | LAQLLLILSHIR | 1388.89 | 2 | 695.451 | 738.462 | y6 |
| | | | 2 | 695.451 | 851.546 | y7 |
| | | | 2 | 695.451 | 964.63 | Y8 |
| | | | 2 | 695.451 | 1077.714 | y9 |
| SEQ ID NO: 2 | LLFAPNLLLDR | 1283.76 | 2 | 642.887 | 840.493 | y7 |
| | | | 2 | 642.887 | 911.53 | Y8 |
| | | | 2 | 642.887 | 1058.599 | y9 |
| SEQ ID NO: 3 | AGLTLQQQHQR | 1278.68 | 2 | 640.347 | 696.353 | y5 |
| | | | 2 | 640.347 | 824.412 | y6 |
| | | | 2 | 640.347 | 937.496 | y7 |
| | | | 2 | 640.347 | 1038.543 | y8 |
| SEQ ID NO: 4 | VLLLLNTIPLEGLR | 1562.98 | 2 | 782.495 | 684.403 | y6 |
| | | | 2 | 782.495 | 898.535 | y8 |
| | | | 2 | 782.495 | 1012.578 | y9 |
| | | | 2 | 782.495 | 1125.662 | y10 |
| SEQ ID NO: 5 | VGDSSGTAAAHK | 1099.53 | 2 | 550.77 | 598.33 | y6 |
| | | | 2 | 550.77 | 655.352 | y7 |
| | | | 2 | 550.77 | 742.384 | y8 |
| | | | 2 | 550.77 | 829.416 | y9 |
| | | | 2 | 550.77 | 944.443 | y10 |
| SEQ ID NO: 6 | LDLTENLTGSK | 1189.62 | 2 | 595.817 | 619.34 | y6 |
| | | | 2 | 595.817 | 748.383 | y7 |
| | | | 2 | 595.817 | 849.431 | y8 |
| | | | 2 | 595.817 | 962.515 | y9 |
| SEQ ID NO: 7 | VEPVGDVVSTR | 1156.61 | 2 | 579.312 | 561.335 | y5 |
| | | | 2 | 579.312 | 733.383 | y7 |
| | | | 2 | 579.312 | 832.452 | y8 |
| | | | 2 | 579.312 | 929.505 | y9 |

The ER, PR, and/or Ki67 tryptic peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the ER, PR, and/or Ki67 proteins in formalin fixed tissue. Further data analysis of these experiments indicated no preference is observed for any specific peptides from any specific organ site. Thus, each of these peptides is believed to be suitable for conducting SRM/MRM assays of the ER, PR, and/or Ki67 proteins on a Liquid Tissue™ lysate from any formalin fixed tissue originating from any biological sample or from any organ site in the body.

One consideration for conducting an SRM/MRM assay is the type of instrument that may be employed in the analysis of the peptides. Although SRM/MRM assays can be developed and performed on any type of mass spectrometer, including a MALDI, ion trap, or triple quadrupole, the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement an SRM/MRM assay for each peptide derived from the ER, PR, and/or Ki67 proteins it is desirable to utilize information in addition to the peptide sequence in the analysis. That additional information may be used in directing and instructing the mass spectrometer (e.g. a triple quadrupole mass spectrometer), to perform the correct and focused analysis of specific targeted peptide(s), such that the assay may be effectively performed.

The additional information about target peptides in general, and about specific ER, PR, and/or Ki67 peptides, may include one or more of the mono isotopic mass of the peptide, its precursor charge state, the precursor m/z value, the m/z transition ions, and the ion type of each transition ion. Table 2 shows additional information for some peptides shown in Table 1 that may be used to develop an SRM/MRM assay for the ER, PR, and/or Ki67 proteins.

The methods described below can be used to: 1) identify candidate peptides from the ER, PR, and/or Ki67 proteins that can be used for a mass spectrometry-based SRM/MRM assay for the ER, PR, and/or Ki67 proteins, 2) develop individual SRM/MRM assays, or multiplexed assays, for target peptides from the ER, PR, and/or Ki67 proteins in order to correlate to breast cancer, and 3) apply quantitative assays to breast cancer diagnosis and/or choice of optimal therapy for breast cancer, and any other cancer analyzed by described SRM/MRM assays.

Assay Methods

I. Identification of SRM/MRM Candidate Fragment Peptides for the ER, PR, and/or Ki67 Proteins:
   a. Prepare a Liquid Tissue™ protein lysate from a formalin fixed biological sample using a protease or proteases, (that may or may not include trypsin), to digest proteins
   b. Analyze all protein fragments in the Liquid Tissue™ lysate on an ion trap tandem mass spectrometer and identify all fragment peptides from the ER, PR, and/or Ki67 proteins, where individual fragment peptides do not contain any peptide modifications such as phosphorylations or glycosylations
   c. Analyze all protein fragments in the Liquid Tissue™ lysate on an ion trap tandem mass spectrometer and identify all fragment peptides from the ER, PR, and/or Ki67 proteins that carry peptide modifications such as for example phosphorylated or glycosylated residues
   d. All peptides generated by a specific digestion method from the entire, full length ER, PR, and/or Ki67 proteins potentially can be measured, but preferred peptides used for development of the SRM/MRM assay are those that are identified by mass spectrometry directly in a complex Liquid Tissue™ protein lysate prepared from a formalin fixed biological sample
   e. Peptides that are specifically modified (phosphorylated, glycosylated, etc.) in patient tissue and which ionize, and thus detected, in a mass spectrometer when analyzing a Liquid Tissue™ lysate from a formalin fixed biological sample are identified as candidate peptides for assaying peptide modifications of the ER, PR, and/or Ki67 proteins II. Mass Spectrometry Assay for Fragment Peptides from ER, PR, and/or Ki67 Proteins
   a. SRM/MRM assay on a triple quadrupole mass spectrometer for individual fragment peptides identified in a Liquid Tissue™ lysate is applied to peptides from the ER, PR, and/or Ki67 proteins
     i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
     ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
     iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
   b. Perform SRM/MRM analysis so that the amount of the fragment peptide of the ER, PR, and/or Ki67 proteins that is detected, as a function of the unique SRM/MRM signature peak area from an SRM/MRM mass spectrometry analysis, can indicate both the relative and absolute amount of the ER, PR, and/or Ki67 proteins in a particular protein lysate.
     i. Relative quantitation may be achieved by:
       1. Determining increased or decreased presence of the ER, PR, and/or Ki67 proteins by comparing the SRM/MRM signature peak area from a given ER, PR, and/or Ki67 peptide detected in a Liquid Tissue™ lysate from one formalin fixed biological sample to the same SRM/MRM signature peak area of the same ER, PR, and/or Ki67 fragment peptide in at least a second, third, fourth or more Liquid Tissue™ lysates from least a second, third, fourth or more formalin fixed biological samples.
       2. Determining increased or decreased presence of the ER, PR, and/or Ki67 proteins by comparing the SRM/MRM signature peak area from a given ER, PR, and/or Ki67 peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
       3. Determining increased or decreased presence of the ER, PR, and/or Ki67 proteins by comparing the SRM/MRM signature peak area for a given ER, PR, and/or Ki67 peptide to the SRM/MRM signature peak areas from other fragment peptides derived from different proteins within the same Liquid Tissue™ lysate from the formalin fixed biological sample in order to normalize changing levels of ER, PR, and/or Ki67 proteins to levels of other proteins that do not change their levels of expression under various cellular conditions.
       4. These assays can be applied to both unmodified fragment peptides and for modified fragment peptides of the ER, PR, and/or Ki67 proteins, where the modifications include but are not limited to phosphorylation and/or glycosylation, and where the relative levels of modified peptides are determined in the same manner as determining relative amounts of unmodified peptides.
    ii. Absolute quantitation of a given peptide may be achieved by comparing the SRM/MRM signature peak area for a given fragment peptide from the ER, PR, and/or Ki67 proteins in an individual biological sample to the SRM/MRM signature peak area of an internal fragment peptide standard spiked into the protein lysate from the biological sample.
        1. The internal standard is a labeled synthetic version of the fragment peptide from the ER, PR, and/or Ki67 proteins that is being interrogated. This standard is spiked into a sample in known amounts, and the SRM/MRM signature peak area can be determined for both the internal fragment peptide standard and the native fragment peptide in the biological sample separately, followed by comparison of both peak areas.
        2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
III. Apply Fragment Peptide Quantitation to Cancer Diagnosis and Treatment
    a. Perform relative and/or absolute quantitation of fragment peptide levels of the ER, PR, and/or Ki67 proteins and demonstrate that the previously-determined association, as well understood in the field of cancer, of ER, PR, and/or Ki67 protein expression to the stage/grade/status of cancer in patient tumor tissue is confirmed.
    b. Perform relative and/or absolute quantitation of fragment peptide levels of the ER, PR, and/or Ki67 proteins individually, in combinations, or all simultaneously, and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy.

The information shown in Table 2 is desirable to develop an SRM/MRM assay for quantitation of the ER, PR, and/or Ki67 proteins on a triplequadrupole mass spectrometer. Specific and unique characteristics about these ER, PR, and/or Ki67 peptides were developed by analysis of all ER, PR, and/or Ki67 peptides on an ion trap and/or triple quadrupole mass spectrometers. That information includes the monoisotopic mass of the peptide, its precursor charge state, the precursor m/z value, the transition m/z values of the precursor, and the ion types of each of the identified transitions. That information must be determined experimentally for each and every candidate SRM/MRM peptide directly in Liquid Tissue™ lysates from formalin fixed tissue; because, interestingly, not all peptides from the ER, PR, and/or Ki67 proteins can be detected in such lysates using SRM/MRM as described herein, indicating that ER, PR, and/or Ki67 peptides not detected cannot be considered candidate peptides for developing an SRM/MRM assay for use in quantitating peptides/proteins directly in Liquid Tissue™ lysates from formalin fixed tissue.

Utilizing this information, quantitative SRM/MRM assays can be developed for the ER, PR, and/or Ki67 proteins, and assessment of ER, PR, and/or Ki67 protein levels in tissues based on analysis of formalin fixed breast cancer patient-derived tissue can provide diagnostic, prognostic, and therapeutically-relevant information about each particular breast cancer patient and/or cancer patient that has a different cancer that is not breast cancer.

In one embodiment, this disclosure describes a method for measuring the level of the ER, PR, and/or Ki67 proteins in a biological sample, comprising detecting and/or quantifying the amount of one or more modified or unmodified ER, PR, and/or Ki67 fragment peptides in a protein digest prepared from the biological sample using mass spectrometry; and calculating the level of modified or unmodified ER, PR, and/or Ki67 proteins in the sample; and wherein the level is a relative level or an absolute level. In a related embodiment, this disclosure provides a method for quantifying one or more ER, PR, and/or Ki67 fragment peptides, wherein the method comprises determining the amount of one or more of the ER, PR, and/or Ki67 fragment peptides in a biological sample by comparison to an added internal standard peptide of known amount, wherein each of the ER, PR, and/or Ki67 fragment peptides in the biological sample is compared to an internal standard peptide having the same amino acid sequence. In some embodiments the internal standard is an isotopically labeled internal standard peptide comprising one or more heavy stable isotopes selected from $^{18}O$, $^{17}O$, $^{34}S$, $^{15}N$, $^{13}C$, $^{2}H$ or combinations thereof.

The methods for measuring levels of the ER, PR, and/or Ki67 proteins in a biological sample described herein (or fragment peptides as surrogates thereof) are useful as diagnostic indicators of cancer in a patient or subject. In one embodiment, the results from the measurements of levels of the ER, PR, and/or Ki67 protein may be employed to determine the diagnostic stage/grade/status of a breast cancer, or another cancer that is not of breast origin, by correlating (e.g., comparing) the level of ER, PR, and/or Ki67 proteins found in a tissue with the level of these proteins found in normal and/or cancerous or precancerous tissues.

Embodiments

1. A method for measuring the amount of the ER, PR, and/or Ki67 proteins in a biological sample, comprising detecting and/or quantifying the amount of one or more modified or unmodified ER, PR, and/or Ki67 fragment peptides in a protein digest prepared from the biological sample using mass spectrometry; and calculating the amount of modified or unmodified ER, PR, and/or Ki67 proteins in the sample; and wherein the amount is a relative amount or an absolute amount.
2. The method of embodiment 1, further comprising the step of fractionating the protein digest prior to detecting and/or quantifying the amount of one or more modified or unmodified ER, PR, and/or Ki67 fragment peptides.
3. The method of embodiment 2, wherein the fractionating step is selected from the group consisting of gel electrophoresis, liquid chromatography, capillary electrophoresis, nano-reversed phase liquid chromatography, high performance liquid chromatography, and reverse phase high performance liquid chromatography.

4. The method of any of embodiments 1 to 3, wherein the protein digest of the biological sample is prepared by the Liquid Tissue™ protocol.
5. The method of any of embodiments 1 to 3, wherein the protein digest comprises a protease digest.
6. The method of embodiment 5, wherein the protein digest comprises a trypsin digest.
7. The method of any of embodiments 1 to 6, wherein the mass spectrometry comprises tandem mass spectrometry, ion trap mass spectrometry, triple quadrupole mass spectrometry, MALDI-TOF mass spectrometry, MALDI mass spectrometry, or time of flight mass spectrometry, or any combination thereof
8. The method of embodiment 7, wherein the mode of mass spectrometry used is Selected Reaction Monitoring (SRM), Multiple Reaction Monitoring (MRM), or multiple Selected Reaction Monitoring (mSRM), or any combination thereof
9. The method of any of embodiments 1 to 8, wherein the one or more modified or unmodified ER, PR, and/or Ki67 fragment peptides comprise two, three, four, five, six, seven, eight, nine or ten different amino acid sequence independently selected from those set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.
10. The method of any of embodiments 1 to 9, wherein the biological sample is a blood sample, a urine sample, a serum sample, an ascites sample, a sputum sample, lymphatic fluid, a saliva sample, a cell, or a solid tissue.
11. The method of embodiment 10, wherein the tissue is formalin fixed tissue.
12. The method of embodiment 10 or 11, wherein the tissue is paraffin embedded tissue.
13. The method of embodiment 10, wherein the tissue is obtained from a tumor.
14. The method of embodiment 13, wherein the tumor is a primary tumor.
15. The method of embodiment 13, wherein the tumor is a secondary tumor.
16. The method of any of embodiments 1 to 15, further comprising quantifying a modified or unmodified ER, PR, and/or Ki67 fragment peptide.
17. The method of embodiment 16, wherein quantifying a modified or unmodified fragment peptide comprises comparing the amount of one or more ER, PR, and/or Ki67 fragment peptides comprising an amino acid sequence of about 8 to about 45 amino acid residues of ER, PR, and/or Ki67 as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10 in one biological sample to the amount of the same ER, PR, and/or Ki67 fragment peptide in a different and separate biological sample.
18. The method of embodiment 17, wherein quantifying one or more modified or unmodified ER, PR, and/or Ki67 fragment peptides comprises determining the amount of each of said one or more ER, PR, and/or Ki67 fragment peptides in a biological sample by comparison to an added internal standard peptide of a known amount, wherein each of the ER, PR, and/or Ki67 fragment peptides in the biological sample is compared to an internal standard peptide having the same amino acid sequence.
19. The method of embodiment 18, wherein the internal standard peptide is an isotopically labeled peptide.
20. The method of embodiment 19, wherein the isotopically labeled internal standard peptide comprises one or more heavy stable isotopes selected from the group consisting of $^{18}O$, $^{17}O$, $^{34}S$, $^{15}N$, $^{13}C$, and $^{2}H$, or any combinations thereof.
21. The method of any of embodiments 1 to 20, wherein detecting and/or quantifying the amount of one or more modified or unmodified ER, PR, and/or Ki67 fragment peptides in the protein digest indicates the presence of modified or unmodified ER, PR, and/or Ki67 proteins and an association with cancer, and in particular breast cancer, in the subject.
22. The method of embodiment 21, further comprising correlating the results of detecting and/or quantifying amounts of one or more modified or unmodified ER, PR, and/or Ki67 fragment peptides, or the amount of the ER, PR, and/or Ki67 proteins to the diagnostic stage/grade/status of the cancer.
23. The method of embodiment 22, wherein correlating the results of detecting and/or quantifying the amount of one or more modified or unmodified ER, PR, and/or Ki67 fragment peptides, or the amount of the ER, PR, and/or Ki67 protein to the diagnostic stage/grade/status of the cancer is combined with detected and/or quantified amounts of other proteins, or peptides from other proteins, in a multiplex format to provide additional information about the diagnostic stage/grade/status of the cancer.
24. The method of any one of embodiments 1 to 23, further comprising selecting for the subject, from which the biological sample is obtained, a treatment based on the presence, absence, or amount of one or more ER, PR, and/or Ki67 fragment peptides or the amount of ER, PR, and/or Ki67 proteins.
25. The method of any one of embodiments 1 to 24, further comprising administering to the patient, from which the biological sample is obtained, a therapeutically effective amount of a therapeutic agent, wherein the therapeutic agent and/or amount of the therapeutic agent administered is based upon the amount of one or more modified or unmodified ER, PR, and/or Ki67 fragment peptides or the amount of ER, PR, and/or Ki67 proteins.
26. The method of embodiments 24 or 25, wherein the treatment or the therapeutic agent is directed to cancer cells expressing ER, PR, and/or Ki67 proteins.
27. The method of any of embodiments 1 to 26, wherein the biological sample is formalin fixed tumor tissue that has been processed for quantifying the amount of one or more modified or unmodified ER, PR, and/or Ki67 fragment peptides employing the Liquid Tissue™ protocol and reagents.
28. The method of any of embodiments 1-27, wherein said one or more modified or unmodified ER, PR, and/or Ki67 fragment peptides is one or more, two or more, three or more, four or more, five or more, or six or more of the peptides in Table 1.
29. The method of any of embodiments 1-28, comprising quantifying the amount of one, two, three, four, five, six, or seven of the peptides in Table 2.
30. A composition comprising one, two, three, four, five, six, seven, eight, nine, or ten of the peptides in Table 1 or antibodies thereto, said composition optionally excluding one, two, three, four, five, or more peptides of ER, PR, and/or Ki67 that are not peptides of SEQ ID NOs: 1, 2, 3, 4, 5, 6, 7, 8, 9, or 10.
31. The composition of embodiment 30, comprising one, two, three, four, five, six, or seven of the peptides of Table 2 or antibodies thereto, said composition optionally excluding one, two, three, four, five, or more peptides of ER, PR, and/or Ki67 that are not peptides of SEQ ID NOs: 1, 2, 3, 4, 5, 6, or 7.

It is to be understood that the description, specific examples and data, while indicating exemplary aspects, are given by way of illustration and are not intended to limit the present disclosure. Various changes and modifications within the present disclosure will become apparent to the skilled artisan from the discussion, detailed description and data contained herein, and thus are considered part of the subject matter of this application.

The invention claimed is:

1. A method for measuring the amount of the Ki67 protein in a biological sample of formalin-fixed tissue, comprising detecting and quantifying the amount of a Ki67 fragment peptide in a protein digest prepared from said biological sample using mass spectrometry; and calculating the amount of Ki67 protein in said sample; wherein said Ki67 fragment peptide is the peptide of SEQ ID NO:6 or SEQ ID NO:7 and wherein the amount is a relative amount or an absolute amount.

2. The method of claim 1, further comprising the step of fractionating the protein digest prior to detecting and quantifying the amount of said Ki67 fragment peptide.

3. The method of claim 1, wherein the protein digest comprises a protease digest.

4. The method of claim 3, wherein the protein digest comprises a trypsin digest.

5. The method of claim 1, wherein the tissue is paraffin embedded tissue.

6. The method of claim 1, wherein the tissue is obtained from a tumor.

7. The method of claim 1, wherein quantifying said fragment peptide comprises comparing the amount of said fragment peptide in one biological sample to the amount of the same Ki67 fragment peptide in a different and separate biological sample.

8. The method of claim 7, wherein quantifying said fragment peptide comprises determining the amount of said fragment peptide in a biological sample by comparison to an added internal standard peptide of a known amount having the same amino acid sequence.

9. The method of claim 1, wherein detecting and quantifying the amount of said Ki67 fragment peptide in the protein digest indicates the presence of modified or unmodified Ki67 protein and an association with cancer in the subject.

10. The method of claim 9, further comprising correlating the results of detecting and quantifying amounts of said Ki67 fragment peptide, or the amount of the protein to the diagnostic stage/grade/status of the cancer.

11. The method of claim 10, wherein correlating the results of detecting and quantifying the amount of said Ki67 fragment peptide, or the amount of the Ki67 protein to the diagnostic stage/grade/status of the cancer is combined with detected and/or quantified amounts of other proteins, or peptides from other proteins, in a multiplex format to provide additional information about the diagnostic stage/grade/status of the cancer.

12. The method of claim 1, further comprising administering to the patient, from which the biological sample is obtained, a therapeutically effective amount of a therapeutic agent, wherein the therapeutic agent and/or amount of the therapeutic agent administered is based upon the amount of said Ki67 fragment peptide or the amount of Ki67 protein.

13. The method of claim 12, wherein the treatment or the therapeutic agent is directed to cancer cells expressing Ki67 protein.

14. The method of claim 1, further comprising detecting and/or quantifying the amount of at least one additional fragment peptide selected from the group consisting of ER and PR fragment peptides in said protein digest using mass spectrometry; and calculating the amount of ER and/or PR protein in said sample; and wherein the amount is a relative amount or an absolute amount.

15. The method of claim 14, wherein said additional fragment peptide is a ER fragment peptide.

16. The method of claim 14, wherein said additional fragment peptide is a PR fragment peptide.

17. The method of claim 1, wherein said fragment peptide is the peptide of SEQ ID NO:7.

* * * * *